(12) United States Patent
Kipper et al.

(10) Patent No.: US 9,597,434 B2
(45) Date of Patent: Mar. 21, 2017

(54) SURFACE TREATMENTS FOR VASCULAR STENTS AND METHODS THEREOF

(71) Applicants: COLORADO STATE UNIVERSITY RESEARCH FOUNDATION, Fort Collins, CO (US); Matthew Kipper, Fort Collins, CO (US); Ketul Popat, Fort Collins, CO (US); Melissa Reynolds, Fort Collins, CO (US); Victoria Leszczak, Fort Collins, CO (US); Raimundo Romero, Fort Collins, CO (US)

(72) Inventors: Matthew Kipper, Fort Collins, CO (US); Ketul Popat, Fort Collins, CO (US); Melissa Reynolds, Fort Collins, CO (US); Victoria Leszczak, Fort Collins, CO (US); Raimundo Romero, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 14/783,895

(22) PCT Filed: Apr. 14, 2014

(86) PCT No.: PCT/US2014/034027
§ 371 (c)(1),
(2) Date: Oct. 12, 2015

(87) PCT Pub. No.: WO2014/169281
PCT Pub. Date: Oct. 16, 2014

(65) Prior Publication Data
US 2016/0067388 A1    Mar. 10, 2016

Related U.S. Application Data

(60) Provisional application No. 61/811,574, filed on Apr. 12, 2013.

(51) Int. Cl.
| | | |
|---|---|---|
| A61F 2/00 | (2006.01) | |
| A61L 31/10 | (2006.01) | |
| A61L 31/16 | (2006.01) | |
| A61L 31/02 | (2006.01) | |
| B05D 7/00 | (2006.01) | |
| C25D 11/26 | (2006.01) | |

(52) U.S. Cl.
CPC ............. *A61L 31/10* (2013.01); *A61L 31/022* (2013.01); *A61L 31/16* (2013.01); *B05D 7/58* (2013.01); *C25D 11/26* (2013.01); *A61L 2300/114* (2013.01); *A61L 2300/236* (2013.01); *A61L 2300/252* (2013.01); *A61L 2300/414* (2013.01); *A61L 2300/45* (2013.01); *A61L 2300/606* (2013.01); *A61L 2300/61* (2013.01); *A61L 2400/12* (2013.01); *A61L 2400/18* (2013.01); *A61L 2420/02* (2013.01); *A61L 2420/08* (2013.01)

(58) Field of Classification Search
None
See application file for complete search history.

(56) References Cited

U.S. PATENT DOCUMENTS

| | | | |
|---|---|---|---|
| 2005/0216075 A1 | 9/2005 | Wang et al. | |
| 2008/0175881 A1 | 7/2008 | Ippoliti et al. | |
| 2009/0068244 A1 | 3/2009 | Weber et al. | |
| 2009/0082856 A1 | 3/2009 | Flanagan | |
| 2009/0117087 A1 | 5/2009 | Carroll et al. | |
| 2009/0324684 A1 | 12/2009 | Atanasoska et al. | |
| 2010/0028387 A1* | 2/2010 | Balasundaram | A61L 27/06 424/400 |
| 2010/0215712 A1* | 8/2010 | Zhang | A61L 31/022 424/423 |
| 2010/0280452 A1* | 11/2010 | Chen | A61L 29/085 604/103.01 |
| 2011/0021965 A1* | 1/2011 | Karp | A61F 2/0077 602/54 |
| 2012/0136323 A1* | 5/2012 | Stasko | A61L 15/225 604/290 |

OTHER PUBLICATIONS

International Search Report and Written Opinion, PCT/US2014/034027, dated Sep. 23, 2014.
Gribova, V. et al., *Polyelectrolyte Multilayer Assemblies on Materials Surfaces: From Cell Adhestion to Tissue Engineering*. Chemistry of Materials, vol. 24, No. 5, 2012, pp. 854-869.

\* cited by examiner

*Primary Examiner* — Robert A Wax
*Assistant Examiner* — Quanglong Truong
(74) *Attorney, Agent, or Firm* — Polsinelli PC

(57) ABSTRACT

Surface modified medical devices with nanotubes and polyelectrolyte multilayers, methods of promoting endothelialization, and methods of modifying a medical device surface are disclosed. Nanotubes may be formed on the surface of the medical device and may further be coated with polyelectrolyte multilayers of a polycation and a polyanion. The surface modification is characterized by a nanopattern on the surface of the medical device, with biomimetic properties.

39 Claims, 12 Drawing Sheets

SURFACE TREATMENTS FOR VASCULAR STENTS AND METHODS THEREOF

CROSS REFERENCE TO RELATED APPLICATION

This application is a non-provisional that claims benefit to U.S. Provisional Patent Application No. 61/811,574, filed on Apr. 12, 2013, the disclosure of which is herein incorporated by reference in its entirety.

GOVERNMENTAL SUPPORT

This invention was made with government support under Grant No. R21AR057341 awarded by the National Institutes of Health, Grant No. DMR0847641 awarded by National Science Foundation., and Grant No. W81XWH-11-2-0113 awarded by Department of Defense-CDMPR. The government has certain rights in the invention.

FIELD OF THE INVENTION

The present invention relates to surface treatments for medical devices to promote endothelialization without inducing smooth muscle cell proliferation.

BACKGROUND

According to the American Heart Association, approximately 615,000 stent procedures are performed each year in the United States to treat coronary artery disease. The stents used in these procedures fall into two major categories: bare metal stents and drug-eluting stents. Traditional bare metal stents are commonly made from 316L stainless steel, cobalt-based alloys, tantalum, or titanium alloys such as nitinol. These stents are effective in opening up the narrowed arteries in the short-term, however they suffer from high rates of restenosis, with about 30% of patients requiring additional invasive follow-up procedures within 3-6 months of implantation. In the case of drug-eluting stents, the stent surface is coated with a polymer (e.g. polyethylene-co-vinyl acetate (PEVA) and poly n-butyl methacrylate (PBMA)). Cytostatic drugs such as sirolimus or paclitaxel are formulated in the polymer coating such that they can be released though the healing period. These drugs are used as antiproliferative agents to prevent proliferation of SMCs.

Several large clinical studies have demonstrated lower restenosis rates in patients treated with drug-eluting stents when compared to bare metal stents. However, recent studies suggest that drug-eluting stents may increase the risk of late thrombosis leading to increased risk of patient stroke or heart attack. It is hypothesized that degradation of drug-eluting polymer coating leads to incomplete re-endothelialization of vessel lumen. Further, this can also induce inflammation that can activate phagocytic lymphocytes. This inflammation may initiate the clotting cascade, which is one cause of vascular thrombosis. About 20% of the patients with drug-eluting stents suffer from restenosis followed by late thrombosis leading to stent failure. Thus while bare metal stents and drug-eluting stents are effective in treating coronary artery diseases, the existing technologies have several major drawbacks in terms of long-term success. A need remains for improved implantable devices and methods for surface modification of devices for improved performance in vivo.

SUMMARY

One aspect of the present invention encompasses a medical device for promoting endothelialization which includes a body having at least a first surface, a plurality of nanotubes formed on the first surface of the body, and at least one polyelectrolyte layer deposited on the nanotubes. The polyelectrolyte layer includes a polycation layer and a polyanion layer. The nanotubes and the polyelectrolyte layers form a nanopattern on the first surface of the body of the medical device. The medical device may be a vascular stent. At least one of the polycation or polyanion may include nitric oxide-releasing groups. The medical device may release nitric oxide from the surface. The medical device device releases nitric oxide at a rate of about 5 nmol/s to about 500 nmol/s. The medical device releases nitric oxide for a period of at least about 2 to about 3 weeks. The polycation may include nitric oxide-releasing groups. The polyanion may include nitric oxide-releasing groups. The nanotubes may include titanium, a titanium alloy, a titanium oxide, or stainless steel. The polycation may be chitosan. The polyanion may be a glycosaminoglycan. The glycosaminoglycan may be heparin, heparan sulfate, chondroitin sulfate, keratan sulfate, dextran sulfate, a sulfated polysaccharide, or a sulfate-containing polyelectrolyte. The medical device may further include a growth factor adsorbed on the at least one polyelectrolyte layer. The growth factor may be vascular endothelial growth factor (VEGF).

Another aspect of the present invention encompasses a method of promoting endothelialization in a tissue in a subject in need includes implanting a medical device in the tissue. The device includes a body having at least a first surface, a plurality of nanotubes formed on the first surface of the body, and at least one polyelectrolyte layer deposited on the nanotubes. The polyelectrolyte multilayer includes a polycation layer and a polyanion layer. The nanotubes and the polyelectrolyte layers form a nanopattern on the first surface of the body of the medical device. The medical device may be a vascular stent. At least one of the polycation or polyanion may include nitric oxide-releasing groups. The surface of the device releases nitric oxide over a period of time. The device releases nitric oxide at a rate of about 5 nmol/s to about 500 nmol/s. The device releases nitric oxide for a period of at least about 2 to about 3 weeks. The amount of nitric oxide released by the device over the period of time corresponds to a reduction in a reference dosage amount of a different oxide releasing agent administered to the subject required to achieve a predetermined physiological effect in the subject. The predetermined physiological effect comprises a reduction in platelet activation. The polycation may include nitric oxide-releasing groups. The polyanion may include nitric oxide-releasing groups. The nanotubes may include titanium, a titanium alloy, a titanium oxide, or stainless steel. The polycation may be chitosan. The polyanion may be a glycosaminoglycan. The glycosaminoglycan may be heparin, heparan sulfate, chondroitin sulfate, keratan sulfate, dextran sulfate, a sulfated polysaccharide, or a sulfate-containing polyelectrolyte. The medical device further includes a growth factor adsorbed on to the at least one polyelectrolyte layer. The growth factor may be VEGF.

Another aspect of the present invention encompasses a method of modifying a surface of a medical device to promote (re)endothelialization. The method includes forming nanotubes on at least a first surface of the medical device and depositing at least one polyelectrolyte layer on the nanotubes. The at least one polyelectrolyte multilayer is formed by depositing a polycation layer on the nanotubes, rinsing the surface, depositing a polyanion layer on the nanotubes, and rinsing the surface. The nanotubes and the polyelectrolyte layers form a nanopattern on the first surface of the medical device. At least one of the polycation or the polyanion may be modified with nitric oxide-releasing groups. The the surface of the device releases nitric oxide over a period of time. The device releases nitric oxide at a rate of about 5 nmol/s to about 500 nmol/s. The device releases nitric oxide for a period of at least about 2 to about 3 weeks. The amount of nitric oxide released by the device over the period of time corresponds to a reduction in a reference dosage amount of a different oxide releasing agent administered to the subject required to achieve a predetermined physiological effect in the subject. The predetermined physiological effect includes a reduction in platelet activation. Forming the nanotubes may include anodizing the first surface of the medical device. The method may further include repeating the alternation of the polycation layer and polyanion layer until a desired thickness is reached. The nanotubes may include titanium, a titanium alloy, a titanium oxide, or stainless steel. The polycation may be chitosan. The polyanion may be selected from heparin, heparan sulfate, or chondroitin sulfate. The method may further include adsorbing VEGF to the polyelectrolyte layers.

BRIEF DESCRIPTION OF THE DRAWINGS

The following figures illustrate various aspects of the disclosure.

Corresponding reference characters and labels indicate corresponding elements among the views of the drawings. The headings used in the figures should not be interpreted to limit the scope of the claims.

DETAILED DESCRIPTION

Provided herein is a surface modified medical device that includes at least one surface on which metal nanotubes are formed, and polyelectrolyte multilayers formed on the nanotubes. Surprisingly, the resulting structure is characterized by a unique honeycomb-like surface nanopattern. The surface can support multiple biomimetic functions when the device is implanted in a body tissue, and can support endothelialization or re-endothelialization in the tissue. The surface modified medical device may be combined further with nitric oxide releasing compounds and/or growth factors, which can further promote tissue repair and growth in vivo.

As used herein, "subject" refers to any mammal, including humans, non-human primates, and domestic, livestock and exotic animals including, without limitation dogs, cats, horses, cows, sheep, goats, pigs, cows, llamas, etc. In exemplary methods, the subject is a human.

As used herein, the term "tissue" encompasses any tissue in a subject in which promoting endothelialization or re-endothelialization may be beneficial in repair of the tissue or treatment of a disease or disorder in the subject.

As used herein, the term "nanopattern" refers to an organization of nanostructures, such as nanotubes, on a surface that are identifiable by SEM. The nanopattern may remain visible after coating with polyelectrolyte multilayers. It should be understood that the nanopattern may take on a variety of conformations, including but not limited to a honeycomb-like pattern. The nanopattern may be derived from the structure of the nanotubes.

As used herein, a "disorder" encompasses any disease or condition from which a subject suffers, and which may benefit from surgical implantation of a surface modified device according to the present disclosure. It should be understood that a variety of diseases and conditions are contemplated, including but not limited a cardiovascular disease or condition, a gastrointestinal disease and an ophthalmological disease or condition.

As used interchangeably herein, the term "nitric oxide releasing agent" and "NO releasing agent" refer to any compound or composition that has the effect when administered to a subject of promoting release of or formation of nitric oxide and/or decreasing degradation or re-uptake of nitric oxide in a tissue in the subject.

As used herein, the term "nitric oxide releasing compounds" encompasses any compound that serves as an NO donor. Such compounds may be formed by modifying amine groups with cysteine, N-acetyl cysteine, or another thiol containing moiety, which may be followed by S-nitrosation. Nitric oxide releasing compounds include but are not limited to diazeniumdiolates and S-nitrosothiols.

I. Surface Modified Medical Devices

Figure 6:
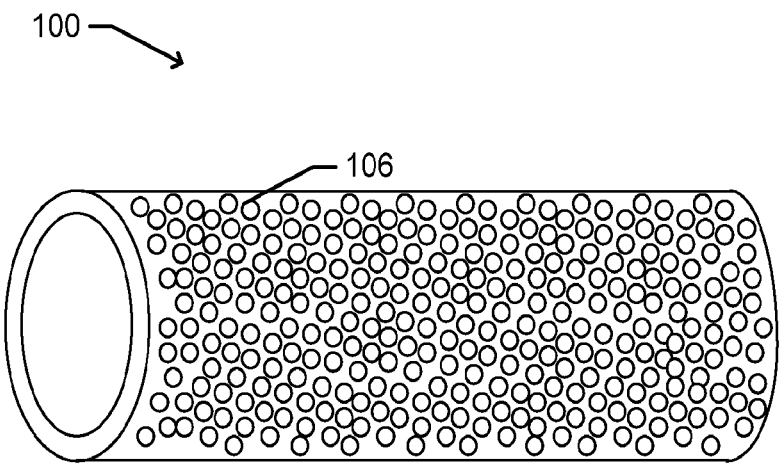
FIG. 6 is an illustrated schematic of a stent with a nanopattern on the outer surface formed by nanotubes and polyelectrolyte multilayers (not to scale).
Figure 7:
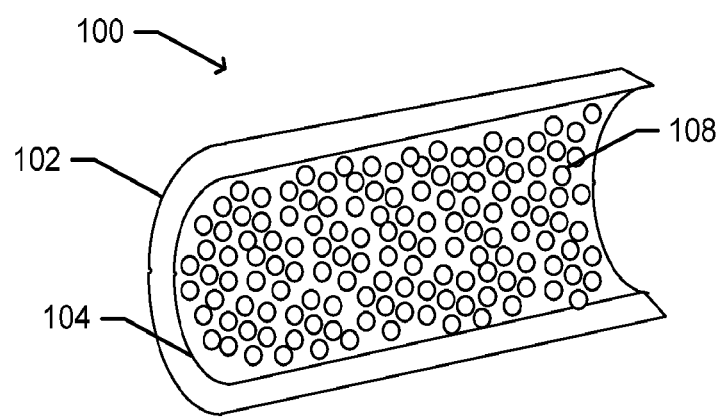
FIG. 7 is an illustrated schematic of a stent with a nanopattern on the inner surface formed by nanotubes and polyelectrolyte multilayers (not to scale).
Figure 8:
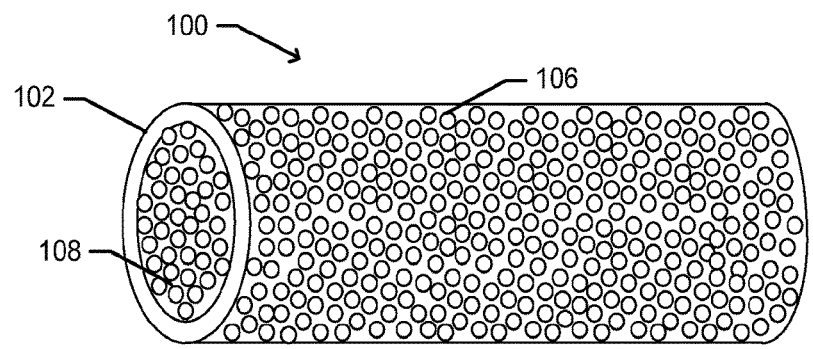
FIG. 8 is an illustrated schematic of a stent with a nanopattern on both the outer surface and the inner surface formed by nanotubes and polyelectrolyte multilayers (not to scale).

In various aspects, the surface modified medical device includes a body of the medical device with at least one surface, nanotubes on the surface of the medical device, and polyelectrolyte multilayers (PEMs) deposited on nanotubes to create a nanopatterned surface. The medical device is generally illustrated as 100 in FIGS. 6-8, with a modified surface 106,108 on the outer wall 102, the inner wall 104, or both. FIG. 6 is an illustrated schematic of a medical device with a nanopattern on the outer surface formed by nanotubes and polyelectrolyte multilayers. FIG. 7 is an illustrated schematic of a medical device with a nanopattern on the inner surface formed by nanotubes and polyelectrolyte multilayers. FIG. 8 is an illustrated schematic of a medical device with a nanopattern on both the outer surface and the inner surface formed by nanotubes and polyelectrolyte multilayers.

A. Medical Devices

At least one surface on the body of a medical device may be modified with nanotubes and PEMs. The medical device may be a metal medical device for implantation into a subject in need. In various aspects, the medical device is in contact with blood when implanted. Such medical devices include, but are not limited to, stents (including coronary vascular stents, peripheral vascular stents, cerebral, utethral, uteral, bilary, tracheal, gastrointestinal and esophageal stents), stent coverings, stent grafts, vascular grafts, vascular access ports, catheters, guide wires, abdominal aortic aneurysm devices, balloons, filters, dialysis ports, embolization devices including cerebral aneurysm filler coils, embolic agents, hermetic sealants, septal defect closure devices, myocardial plugs, patches, pacemakers, lead coatings including coatings for pacemaker leads, defibrillation leads, and coils, ventricular assist devices including left ventricular assist hearts and pumps, total artificial hearts, shunts, an interventional cardiology device, valves including heart valves and vascular valves, anastomosis clips and rings, cochlear implants, tissue bulking devices, cannulae, metal wire ligatures, urethral slings, bone plates, joint prostheses, orthopedic fixation devices such as interference screws in the ankle, knee, and hand areas, tacks for ligament attachment and meniscal repair, rods and pins for fracture fixation, screws and plates for craniomaxillofacial repair, dental implants, a ventricular shunt, as well as various other devices that are implanted or inserted into the body and from which a therapeutic agent may be released.

As used herein, the term "at least a first surface" encompasses any surface of a three-dimensional shape or structure usefully implanted in a body tissue as part of a therapeutic treatment. It should be understood that a variety of shapes and structures are suitable for implantation in body tissues to provide various mechanical functions, and each may include one or more surfaces which can be usefully modified according to the present disclosure, to promote endothelialization or re-endothelialization of a tissue. For example, a first surface of a device such as a stent or catheter may be an interior wall of the device which faces an opening or lumen through the device having a generally cylindrical shape defining a central or longitudinal axis. Alternatively, such a device may be surface modified on an outer wall facing the exterior of the device. Alternatively, such a device may be surface modified on both the inner wall and the outer wall facing the exterior of the device. As shown for example in FIGS. 6-8. FIG. 6 illustrates the outer wall 102 of a device 100 modified with a honeycomb-like nanopattern 106 on the surface. FIG. 7 illustrates the inner wall 104 of a device 100 modified with a honeycomb-like nanopattern 108 on the surface. FIG. 8 illustrates the outer wall 102 and inner wall 104 of a device 100 modified with a honeycomb-like nanopattern 106, 108 on both surfaces.

B. Nanotubes

In an aspect, at least a first surface of the medical device may further be modified with nanotubes prior to the coating of the stent with the polyelectrolyte multilayers. The surface of a titanium, titanium alloy (e.g. nitinol), titanium oxide, or stainless steel material may be modified to produce arrays of nanotubes. Generally nanotubes are hollow, cylindrical nanostructures. The nanotubes may measure about 50 nm to about 500 nm in diameter and about 200 nm to about 50 μm in length. In various aspects, the nanotubes may range in diameter from about 50 nm to about 200 nm, from about 100 nm to about 300 nm, from about 200 nm to about 400 nm, and from about 300 nm to about 500 nm. In various aspects, the nanotubes may range in length from about 200 nm to about 600 nm, from about 400 nm to about 800 nm, from about 600 nm to about 1 μm, from about 800 nm to about 10 μm, from about 5 μm to about 20 μm, from about 10 μm to about 30 μm, from about 20 μm to about 40 μm, and about 30 μm to about 50 μm.

The nanotubes provide tunable nanotopographical features, and the polyelectrolyte multilayers introduce a number of biochemical functions to the surface. Surface nanotopographical features promote surface endothelialization, and organized surface features may help to prevent smooth muscle cell proliferation and increase their differentiation.

Since the cells in vivo are in constant interaction with their surroundings (comprised of pits, protrusion and pores including additional subcellular structures on the nanometer size scale), surface nanoarchitectures similar to that of the natural in vivo environment often elicit enhanced cellular responses. Nanoscale architectures may promote a multitude of cellular responses including improved osseo-integration, augmented mesenchymal stem cell differentiation, enhanced neuronal activation, and increased growth rate of endothelial cells. The nanoscale architectures on implant surfaces suggest a possible correlation with the cellular functionality. The surface modified vascular stent may have improved hemocompatability and immunogenicity compared to present stents and nanomaterials.

C. Polyelectrolyte Multilayers

A surface of the medical device may be coated with polyelectrolyte multilayers (PEMs). In various aspects, the PEMs may be deposited on top of the nanotubes formed on the at least one surface of the medical device. The polyelectrolyte multilayers include at least a polycation layer and a polyanion layer. The PEMs may be phosphonoundecanoic acid and polysaccharide-based polyelectrolyte multilayers in one aspect. The polycation layer and the polyanion layer may be continuously alternated until a desired thickness is reached. The PEMs may include about 2 to about 16 bilayers of a polycation and a polyanion. In various aspects, the PEMs may be about 2, about 4, about 8 and about 16 bilayers of a polycation and a polyanion.

In an aspect, at least the polyanion or the polycation may include functional groups capable of releasing nitric oxide (NO). In one aspect, the number of PEM layers on a titanium nanotube surface may be inversely proportional to the NO release, with an increase in NO release with decreasing number of bilayers. In another aspect, the number of PEM layers on a stainless steel surface may be proportional to the NO release, with an increase in NO release with increasing number of bilayers.

As an example, diazeniumdiolates and S-nitrosothiols are formed on nitrogen and sulfur-based functional groups. The monomer units used to create the biodegradable polymer can be readily modified to incorporate the necessary nitrogen and sulfur based linkers required to allow the structures to be generated that can store and release NO in physiological systems. If multiple therapeutic agents are used, the therapeutic agents can be in the same layer or different layers. Not all of the polyelectrolyte layers used need to have a therapeutic agent. Each layer of the overall polyelectrolyte multilayers may contain a unique combination of zero, one, or multiple therapeutic components.

The polycation may include polysaccharides, such as but not limited to dextran or chitosan. Chitosan promotes the induction of cytokine profiles that lead to the waning of inflammation and healthy integration with the host tissue. In an aspect, the chitosan may be modified with a nitric oxide donating group (NO-chitosan). NO-chitosan may be formed by modifying amine groups in chitosan with cysteine, N-acetyl cysteine, or another thiol containing moiety. This may be followed by S-nitrosation.

Nitric oxide (NO) may be released from the PEMs to improve resistance to thrombosis by preventing platelet activation and adhesion, promoting vasorelaxation, and inhibiting neointimal hyperplasia. The rate of NO release from a surface modified medical device may be from about 0 nmol/s to about 1000 nmol/s. In various aspects, the rate of NO release may be from about 0 nmol/s to about 10 nmol/s, from about 5 nmol/s to about 100 nmol/s, from about 50 nmol/s to about 200 nmol/s, from about 100 nmol/s to about 400 nmol/s, from about 200 nmol/s to about 600 nmol/s, from about 400 nmol/s to about 800 nmol/s, and from about 600 nmol/s to about 1000 nmol/s. In an aspect, the rate NO is released is from about 5 nmol/s to about 500 nmol/s. In one aspect, the flux of NO release from a surface modified medical device may be from about $3 \times 10^{-11}$ to about $1.2 \times 10^{-8}$ mols NO cm-2 min-1. The amount of NO released from the modified surfaces may be in the range of about 40 to about 80 nmoles over a period of at least about 2 hours, for example about 42 to about 77 nmoles in about 2 hours, or any one of about 40, about 45, about 50, about 55, about 60, about 65, about 70, about 75 nmoles over at least about 2 hours. The surface modified medical device may continuously release NO over a period of at least about 2 to about 3 weeks up to at least about 6 weeks.

The polyelectrolyte multilayers may further contain glycosaminoglycans (GAGs), as the polyanion. The polyanion may be but is not limited to heparin, heparan sulfate, chondroitin sulfate, keratan sulfate, dextran sulfate, another sulfated polysaccharide, or a sulfate-containing polyelectrolyte. The anion may be heparin in one aspect, as heparin potentiates the activity of antithrombin III and inhibits blood coagulation.

D. Growth Factors

The polyelectrolyte multilayers may be further modified with therapeutic agents, such as growth factors. A growth factor can be any naturally occurring or synthetic compound capable of stimulating or promoting cell growth, proliferation or differentiation. It should be understood that many growth factors are known and may be used according to the present disclosure. Exemplary growth factors include any growth factor that promotes or enhances endothelial cell growth, proliferation or differentiation.

According the present disclosure, one or more growth factors can be bound to one or more layers of the polyelectrolyte multiplayers. For example, a growth factor may be bound to the polyanion, or to the polycation, or to both. In doing so, the growth factor is stabilized and slowly released from the device surface, in a substantially biomimetic manner. Binding of the growth factor can be achieved for example by exposing the PEM surface to a solution containing the growth factor. In some aspects, the PEM surface may be exposed to the growth factor solution for about 2 hours. In another aspect, the growth factor may be electrostatically adsorbed to the PEMs.

In an aspect, the growth factor may be vascular endothelial growth factor (VEGF), stabilized and presented by the polyanion. Heparin, or other glycosaminoglycans, binds VEGF and its primary receptors, VEGFR1 and VEGFR2. This VEGF and VEGFR binding will help promote endothelialization, by stimulating endothelial cell proliferation, without inducing smooth muscle cell proliferation.

E. Modified Surface Structure

Figure 3:
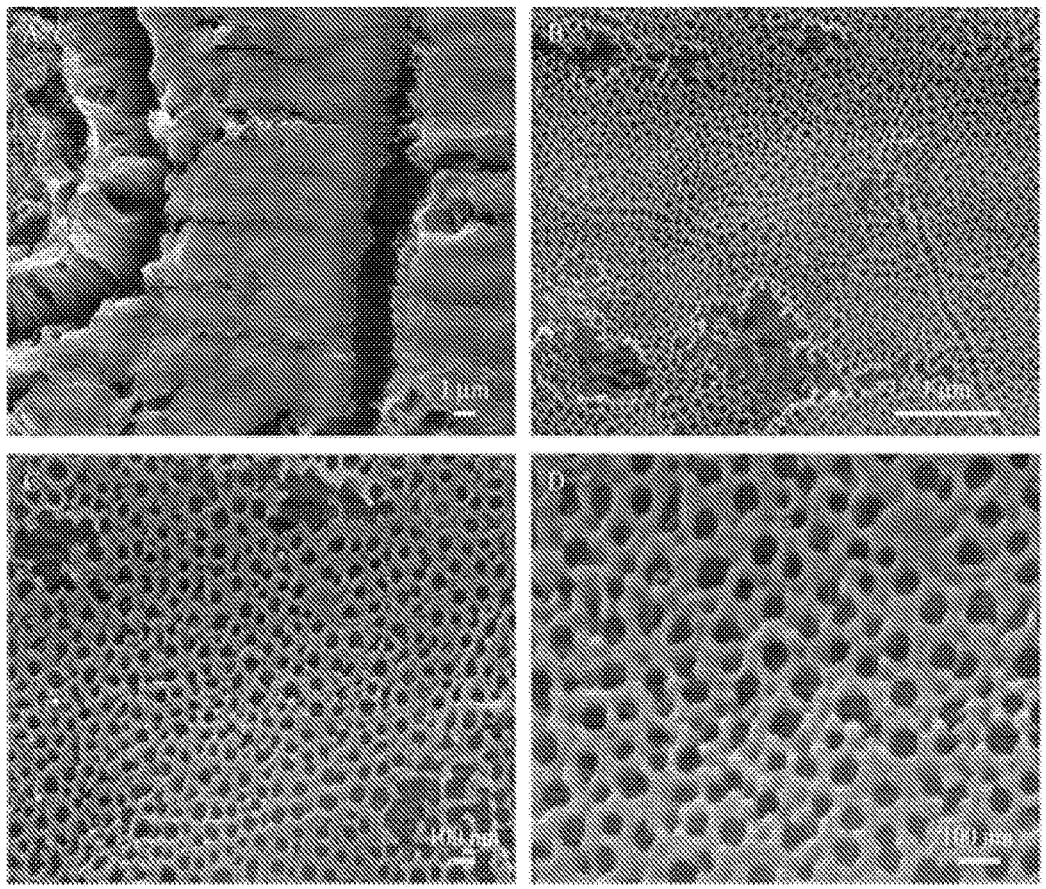
FIG. 3 is SEMs of polyelectrolyte multilayers on titania nanotubes. The nanotubes are 15 μm long and have 50 nm diameter pores. FIGS. A-D show increasing magnification.

Modification of surfaces with polyelectrolyte multilayers typically results in a smooth conformal coating, preserving features of the underlying surface. However, by depositing polyelectrolyte multilayers on nanotubes, the multilayers surprisingly change the orientation of the nanotubes, and the nanotubes, in turn, appear to template a honeycomb-like structure into the polyelectrolyte multilayer, as illustrated for example in FIG. 3. In FIG. 3A, near the left hand side of the image, the sides of the 15 μm-long nanotubes can be seen, as the nanotube array has been "parted" by application of the multilayer. The polyelectrolyte multilayer may exhibit a "honeycomb" like, nanopatterned structure (in FIGS. 3B, 3C, and 3D). Without being limited to a particular theory, the hollow nanotubes may contribute to the honeycomb-like nanopattern when coated with PEMs.

The pores within the honeycomb structure may have regular pores ranging from about 50 nm to about 100 nm in diameter. This honeycomb structure is templated by the underlying nanotubes which have pore diameters of about 50 nm. This porous structure of the polyelectrolyte multilayer is an unexpected feature arising from the polyelectrolyte multilayer assembly on the nanotubes.

Nanotexturing provided by the nanotubes, polysaccharide chemistries, nitric oxide-releasing polymers, and VEGF all promote favorable biological responses. The nanotopography of the nanotubes may promote endothelial cell attachment and inhibit thrombus formation; the chitosan has antimicrobial activity; heparin interacts favorably with enzymes in the coagulation cascade to prevent coagulation; nitric oxide prevents platelet activation and acts as a vasodilator; and VEGF, stabilized by binding to sulfated polysaccharides promotes endothelial cell proliferation, and inhibits smooth muscle cell de-differentiation.

II. Methods of Promoting Endothelialization

Provided herein is a method of promoting endothelialization or re-endothelialization in a tissue, for example re-endothelialization over the surface of a medical device implanted in body tissue. The method may include implanting a medical device that has been modified on at least one surface of the body of the medical device. The modification of the medical device may include nanotubes formed on the surface of the body, and at least one polyelectrolyte layer deposited on the nanotubes. The polyelectrolyte layer may include at least one polycation layer and at least one polyanion layer. The deposition of the PEMs on the nanotubes may form a nanopattern on the surface of the body of the medical device.

As previously described herein, the medical device may be a vascular stent to be implanted in an artery of a subject in need to improve the biocompatibility of the stent while promoting endothelialization and reduce smooth muscle cell (SMC) de-differentiation. In one aspect, the polycation may be chitosan and the polyanion may be heparin, and the polycation and/or the polyanion may or may not be modified with nitric oxide releasing groups. VEGF or another growth factor may further be adsorbed to the PEMs.

Nitric oxide is a well-known naturally-occurring biological agent responsible for maintaining normal hemostasis, cellular signaling, and bone development in the body as well as promoting healthy cell growth and wound healing. Nitric oxide is also responsible for preventing platelet activation and adhesion as well as microbial growth and bacterial invasion of tissue. Nitric oxide also serves as an effecter in wound healing mechanisms, and regulates angiogenesis and revascularization. Functional moieties capable of releasing NO in vivo increase the hemocompatibility of materials by reducing the thrombogenicity. In addition, the release of NO reduces the inflammatory response towards the implanted materials. Thus, nitric oxide has the capability of treating abnormal cell growth while at the same time promoting the healing of surrounding cells. Due to nitric oxide's multiple effects of cells, the incorporation of functional moieties capable for releasing nitric oxide under physiological conditions can impart several advantages to modulating multiple biological processes resulting in healthy incorporation of medical devices into the body, reduction in infection, thrombosis, and monocyte activation, improvement in wound healing at the site of injury, and metathesis of cancerous cells.

The rate of NO release from a surface modified medical device may be from about 0 nmol/s to about 1000 nmol/s. In various aspects, the rate of NO release may be from about 0 nmol/s to about 10 nmol/s, from about 5 nmol/s to about 100 nmol/s, from about 50 nmol/s to about 200 nmol/s, from about 100 nmol/s to about 400 nmol/s, from about 200 nmol/s to about 600 nmol/s, from about 400 nmol/s to about 800 nmol/s, and from about 600 nmol/s to about 1000 nmol/s. In an aspect, the rate NO is released is from about 5 nmol/s to about 500 nmol/s. The amount of NO released from the modified surfaces may be in the range of about 40 to about 80 nmoles over a period of at least about 2 hours, for example about 42 to about 77 nmoles in about 2 hours, or any one of about 40, about 45, about 50, about 55, about 60, about 65, about 70, about 75 nmoles over at least about 2 hours. The surface modified medical device may continuously release NO over a period of at least about 2 to about 3 weeks up to at least about 6 weeks.

The implanted medical device may have an effect on endothelialization, platelet activation, inflammation, or MSC de-differentiation in a tissue when implanted in a subject in need. In an aspect, the patterned surface created by the PEM covered nanotubes may affect the biological properties of the medical device.

II. Methods of Modifying a Medical Device Surface

Figure 5:
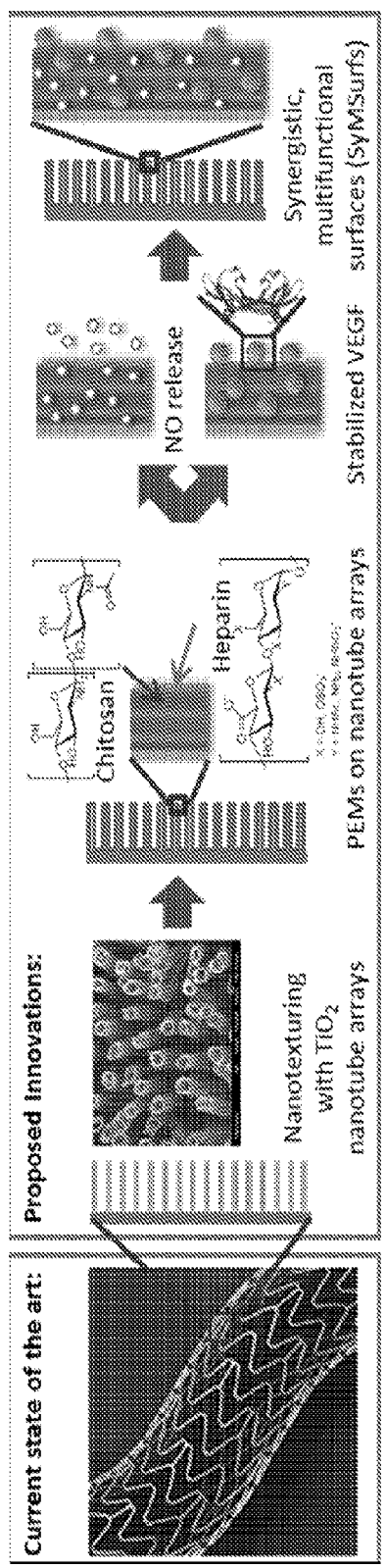
FIG. 5 is an illustration of the modification of a stent with nanotubes on the outer surface coated in polyelectrolyte multilayers with NO release and stabilized VEGF.

Further provided herein is a method for modifying the surfaces of a medical device, generally illustrated in FIG. 5. The method may include modifying a polycation with NO releasing groups and coating a metal stent with alternating layers of a polycation and a polyanion. The metal stent may be further modified by forming nanotubes on the surface of the stent prior to layering the polyelectrolytes and growth factors may be adsorbed onto the polyelectrolyte layers. In other aspects, the method may be extended to other vascular prostheses (e.g. heart valves) and to other blood contacting devices, including biosensors and extracorporeal devices, such as components of hemodialyzers and blood oxygenators.

A. Preparation of Nanotubes

In this process the nanotube diameter and pore size are determined by the anodization voltage and electrolyte composition and pH. Anodization is accompanied by dissolution of titania in an aspect. Competition between the electrochemical etching and the chemical dissolution leads to highly ordered arrays at relatively low potentials. Nanotube architecture can be achieved by anodizing titanium at potentials between about 10 and about 60 V in aqueous electrolyte solutions. The electrolyte solution may include but is not limited to hydrofluoric, hydrofluoric acid and acetic acid, potassium fluoride and sulfuric acid, hydrofluoric acid and nitric acid, and the electrolyte solution may have a pH ranging from about <1 to about 5. The nanotube arrays may then be annealed. In an aspect, the nanotube arrays may be annealed for about 6 hours, with a heating/cooling rate of about 1° C./min from about 250° C. to about 700° C. These are then subsequently modified using the polyelectrolyte multilayer deposition techniques described above.

B. Modification with NO Releasing Groups

Figure 1:
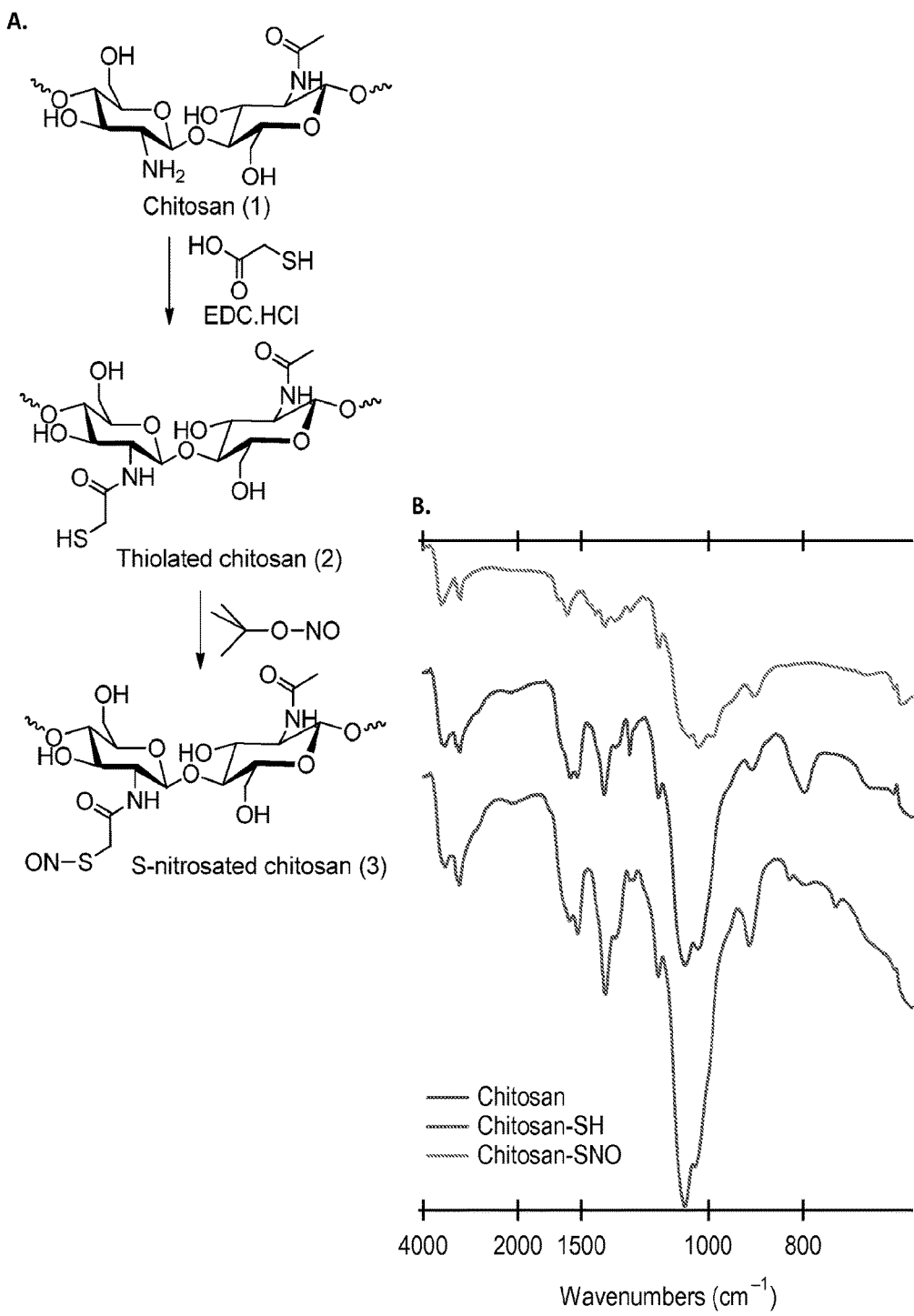
FIG. 1 is a schematic of (FIG. 1A) the synthesis of S-nitrosated chitosan, and (FIG. 1B) FT-IR spectrum of species in all 3 steps in the synthesis shown in FIG. 1A.

In an aspect, at least the polycation or the polyanion may be modified with NO releasing groups. The polycation or polyanion may be modified with S-nitroso thiol. In one aspect, the activation of chitosan with an S-nitroso group is achieved by coupling thioglycolic acid (TGA), N-acetyl cysteine (NAC), and N-acetyl penicillamine (NAP) to the chitosan to form a stable amid bond between the amine in chitosan with the carboxylic acid in the thioglycolic acid, so that chitosan presents a pendent thiol group. The thiol is then reacted with t-butyl nitrite to yield an S-nitrosated chitosan. The synthesis is outlined in FIG. 1. This modification of polycation or polyanion with the S-nitroso functionality may also be performed after the multilayers have been prepared.

C. Deposition of Polyelectrolyte Multilayers

The polycation combined with the polyanion may present a blood-compatible surface. The surface of titanium or titanium-modified with titania nanotubes may be modified via the layer-by-layer deposition of polyelectrolyte multilayers. PEMs may be formed similar to the methods of making PEMs in Almodovar et al., *Macromol. Biosci.* 2011, 11, 72-76 and Almodovar et al., *Biomacromolecules* 2010, 11, 2629-2639 which are hereby incorporated by reference. The process of polyelectrolyte multilayer deposition is illustrated schematically in FIG. 2. In one aspect, the titanium or titania nanotube surfaces are soaked for about 12 to about 24 hours in a 10 mM solution of 11-phosphonoundecanoic acid in dimethylsulfoxide, to activate the surface.

Solutions of the polyanion (for example, heparin, chondroitin sulfate, or another polyanionic glycosaminoglycan) and polycation (for example, chitosan or S-nitrosated chitosan) are prepared in an appropriate aqueous buffer solution. The aqueous buffer may be sodium acetate/acetic acid buffer at about 0.1 to about 0.5 molar and pH between about 4 and about 6.5. A rinse solution may also be prepared, including de-ionized water or a mildly acidic aqueous solution or buffer. The polyanion and polycation solutions are well-dissolved and filtered. The concentration of the polymers should be between about 0.01 M and about 0.5 M on a saccharide unit basis.

The prepared titanium or titania-nanotube surfaces may be exposed to the polycation solution by flowing the solution over the surface, by dipping the surface in the solution, or by agitating the solution containing the surface to be modified. The surface is rinsed by similarly applying the rinse solution. The surface may then be exposed to the polyanion solution, followed by another rinse. This sequence (polycation—rinse—polyanion—rinse) is repeated until the desired number of layers has been adsorbed and the desired thickness has been reached.

The deposition process may be modified to include additional steps in the sequence to introduce additional components, such as a growth factor. In this aspect, the sequence may be polycation—rinse—polyanion—rinse—growth factor—rinse. Alternatively, growth factor might be introduced by first combining the growth factor with the polyanion in solution. In this aspect, the sequence may be polycation—rinse—polyanion/growth factor—rinse). The surface may be stored dry after the deposition of the polyelectrolyte layers.

The deposition of the polycation layer and the polyanion layer may be alternated until a desired thickness or number of layers is reached. In an aspect, the number of bilayers of polycation and polyanion may be about 2, about 4, about 8, and 16 bilayers applied to nanotubes on the surface of the medical device.

D. Modification of the Surfaces

The polyelectrolyte multilayers may be further modified by adsorbing a growth factor to at least one of the PEMs. The surfaces coated with glycosaminoglycan-containing polyelectrolyte multilayers may be exposed to an aqueous solution in which the heparin-binding growth factor is stable. In an aspect, the growth factor is vascular endothelial growth factor (VEGF). The solution of VEGF may be at a concentration ranging from very low (about 1 to about 10 ng/mL) to very high (about 10 to about 100 µg/mL), to tune the amount of growth factor adsorbed to the PEMs. To further control the amount of growth factor and/or the location of the growth factor within the PEMs, the growth factor adsorption may be added to the sequence of steps in the polyelectrolyte multilayer deposition.

EXAMPLES

The examples described herein are included to demonstrate preferred embodiments of the invention. It should be appreciated by those of skill in the art that the techniques disclosed in the examples included herein represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Titania Nanotubes with PEM Deposition on a Vascular Stent

Titania nanotubes were prepared on titanium foil by anodization. Nanotubes were prepared with approximately 50 nm-diameter pores and lengths of 5 µm and 15 µm. Acetate buffer (pH 5.0) was prepared by combining 50 mL of deionized water with 2.30 g sodium acetate and 0.72 mL of glacial acetic acid. 11-Phosphonoundecanoic acid (PUA 0.133 g) was dissolved in 50 mL of dimethylsulfoxide (DMSO) to prepare a 10 millimolar solution. The titanium substrates modified with the titania nanotubes were left to soak in the PUA solution overnight. A "rinse" solution was prepared by dissolving glacial acetic acid in deionized water to obtain a pH 4 solution. A solution of vascular endothelial growth factor (VEGF) was prepared by dissolving 10 µg of VEGF in 10 mL of deionized water. (This stock was separated into 10 1-mL aliquots and stored frozen). One VEGF aliquot was used for this work, and was diluted to 100 ng/mL in deionized water. The chitosan was 80 kDa, 5% acetylated (confirmed by proton NMR) from Novamatrix (Sandvika Norway). The heparin was from Celsus Laboratories (Cincinnati, Ohio) and was 14.4 kDa and 12.5% sulfur.

Chitosan (and nitrosated chitosan) solutions were prepared by adding 0.091 g of chitosan (or NO-chitosan) to 50 mL of acetate buffer and stirring the solutions overnight. Heparin solution was prepared by adding 0.1283 g of heparin sodium to 50 mL of acetate buffer, and stirring until the heparin was dissolved. After dissolution, heparin, chitosan, NO-chitosan and "rinse" solutions were filtered using 0.2 µm PVDF syringe filters.

Figure 2:
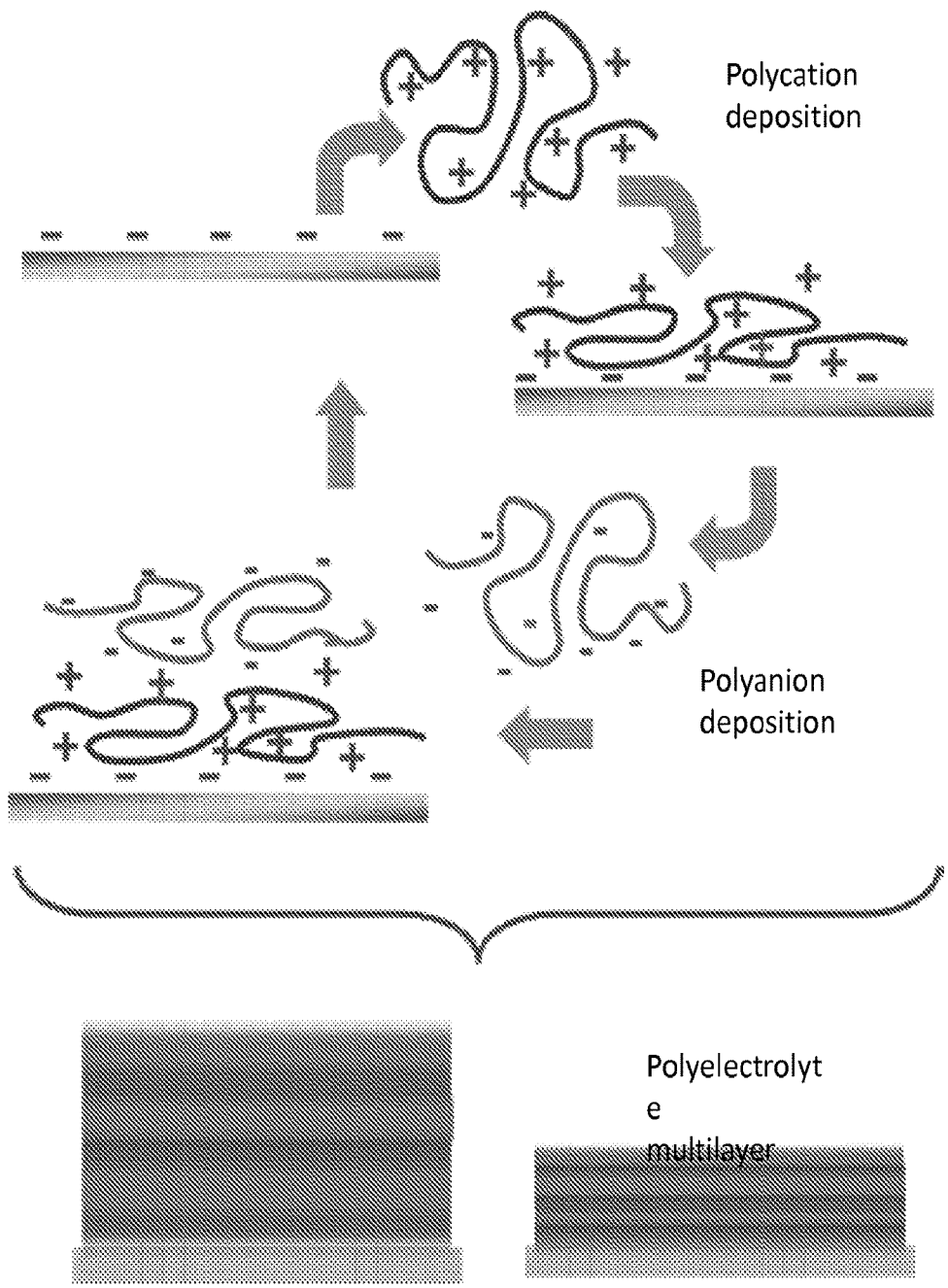
FIG. 2 is an illustration of the polyelectrolyte multilayer deposition.

Polyelectrolyte multilayers were assembled on the titania nanotube surfaces by soaking the surfaces in solutions in the following sequence of steps (each step lasting 5 minutes): chitosan (or NO-chitosan) solution, rinse solution, heparin solution, rinse solution. The method of deposition of the layers is illustrated in FIG. 2. This sequence was repeated three times to make "6-layer" samples, or five times to prepare "10-layer" samples. Following the deposition of the multilayers, the some surfaces were then exposed to the VEGF solution for 2 hours, to allow the VEGF to bind to the heparin-terminated multilayers.

The surfaces were analyzed by drying them in air, and performing X-ray photoelectron spectroscopy (on a Physical Electronics 5800 spectrometer with a monochromatic Al Kα X-ray source and a photoelectron takeoff angle of 45°, analyzer pass energy of 23.5 eV and an X-ray spot size of approximately 800 µm). Some samples were also sputter coated with about 10 nm of gold and imaged by scanning electron microscopy (Jeol JSM 6500F).

Figure 4:
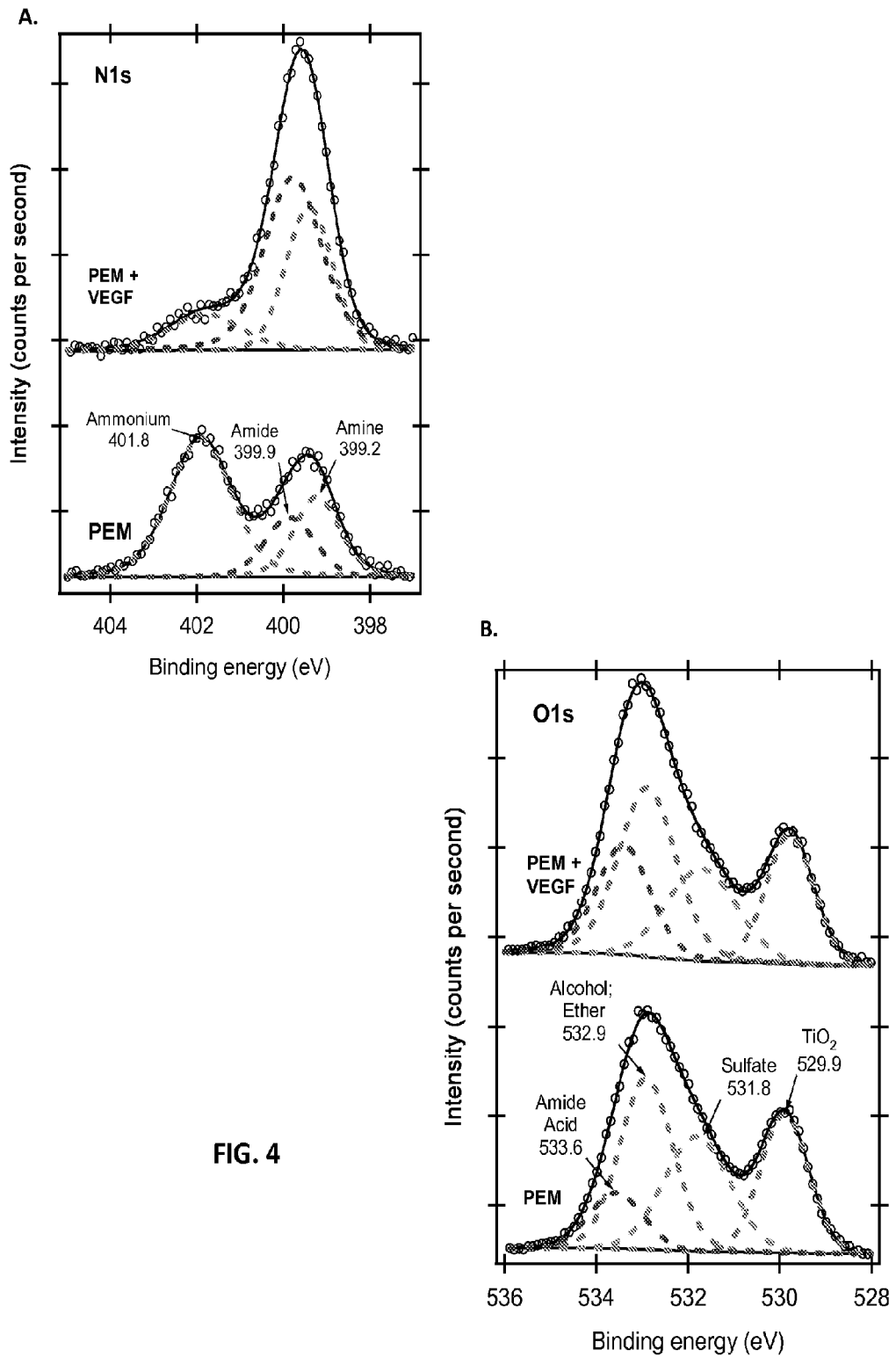
FIGS. 4A-B show N1s and O1s XPS envelopes of PEMs on $TiO_2$ with and without VEGF. Amide peaks demonstrate PEM binding.
FIGS. 4C-D are SEM images of PEMs on $TiO_2$ nanotubes.
Figure 4:
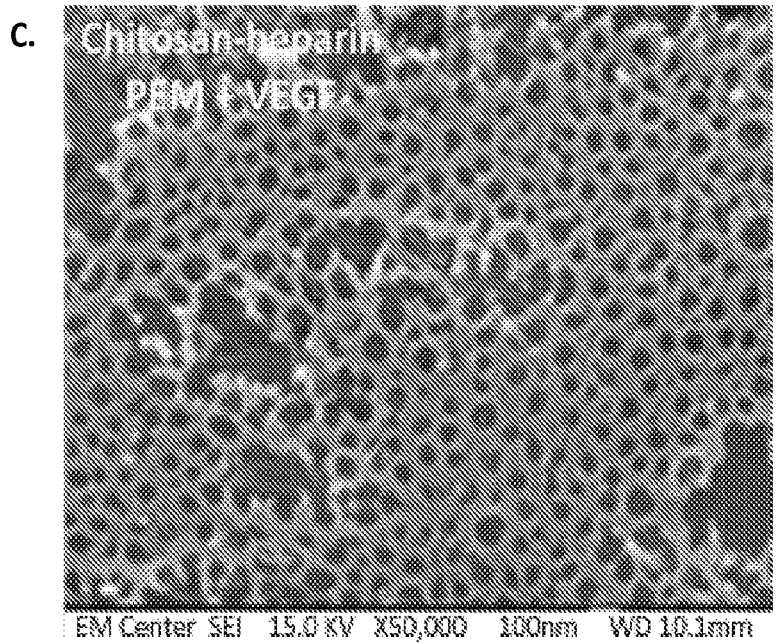
Figure 4:
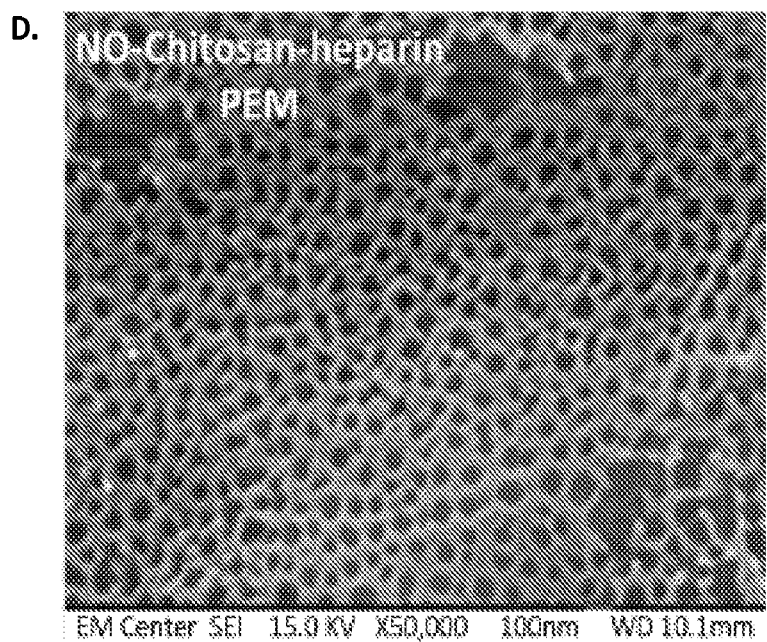

FIG. 4 shows the N1s envelope from a 6-layer chitosan-heparin polyelectrolyte multilayer with (FIG. 4A, top) and without (FIG. 4A, bottom) adsorbed VEGF. The increase in the amide signal is clear indication of substantial VEGF binding to the surface. The O1s envelope (FIG. 4B) also shows a substantial increase in amide signal, confirming VEGF adsorption. The scanning electron micrographs in FIGS. 4C-D show that the same honeycomb-like structure of the PEM may be obtained whether chitosan or NO-chitosan is used as the polycation, and that the structure may be unchanged throughout subsequent aqueous processing steps, (for example, the addition of the VEGF).

Example 2

Nitric-oxide Releasing Layer-by-Layer Coated Stents

Glycocalyx-mimetic surfaces are prepared, to prevent negative blood material interactions by mimicking important features of the endothelial glycocalyx. The combination of polysaccharide-based nanoscale surfaces that mimic the endothelial glycocalyx and the release of a naturally occurring signaling molecule (nitric oxide (NO)) can act synergistically at both the stent-blood and the stent-vessel wall interfaces to truly integrate the stent into the body.

Figure 9:
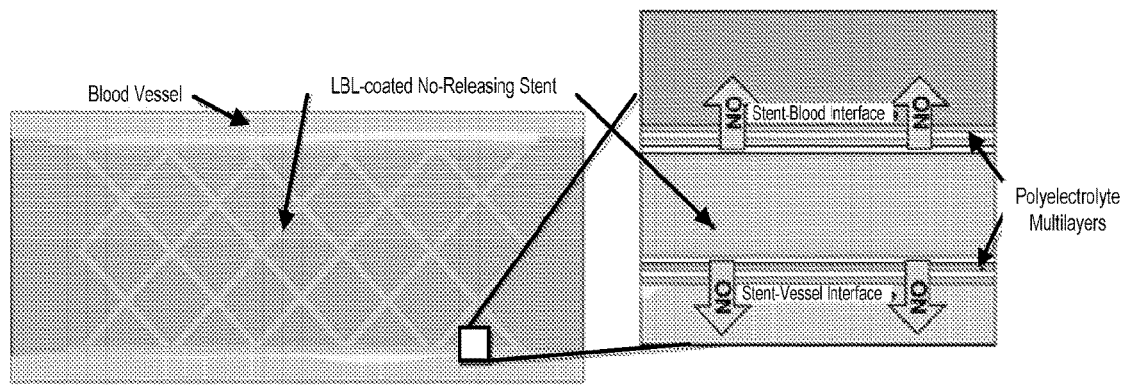
FIG. 9 is a schematic illustration of a longitudinal cross-section of a NO-releasing stent prepared by a layer-by-layer (LBL) coating method and implanted in the lumen of a blood vessel.

A layer-by-layer (LBL) coating method was used to create polyelectrolyte multilayers (PEMs), which incorporate both glycocalyx features and NO release on a stent surface. In addition, the use of two different metal types were tested and compared for their surface structure and ability to release NO. FIG. 9 is a schematic illustration of a longitudinal cross-section of a LBL coated NO-releasing stent implanted in the lumen of a blood vessel, with an expanded view (at right) of the two interfaces between the polyelectrolyte multi players and a) blood, and b) vessel wall.

Figure 10:
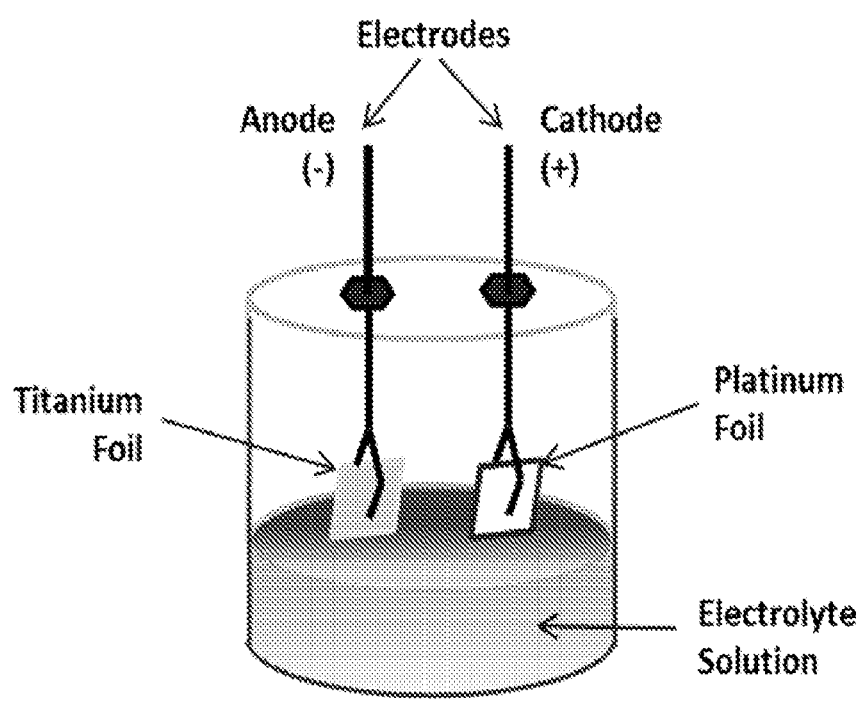
FIG. 10 is a schematic illustration of a method for forming titanium nanotubes as a substrate for an LBL coated stent.

Two different metal substrates were used to prepare stent surfaces. Initially, 1 cm×1 cm metal samples were coated by the layer-by-layer (LBL) method. The first metal substrate was stainless steel 316 (SS). The second metal substrate was titanium, with titanium nanotubes (TiNT) on its surface. Ti-nanotubes were formed as schematically depicted in FIG. 10.

Figure 11:
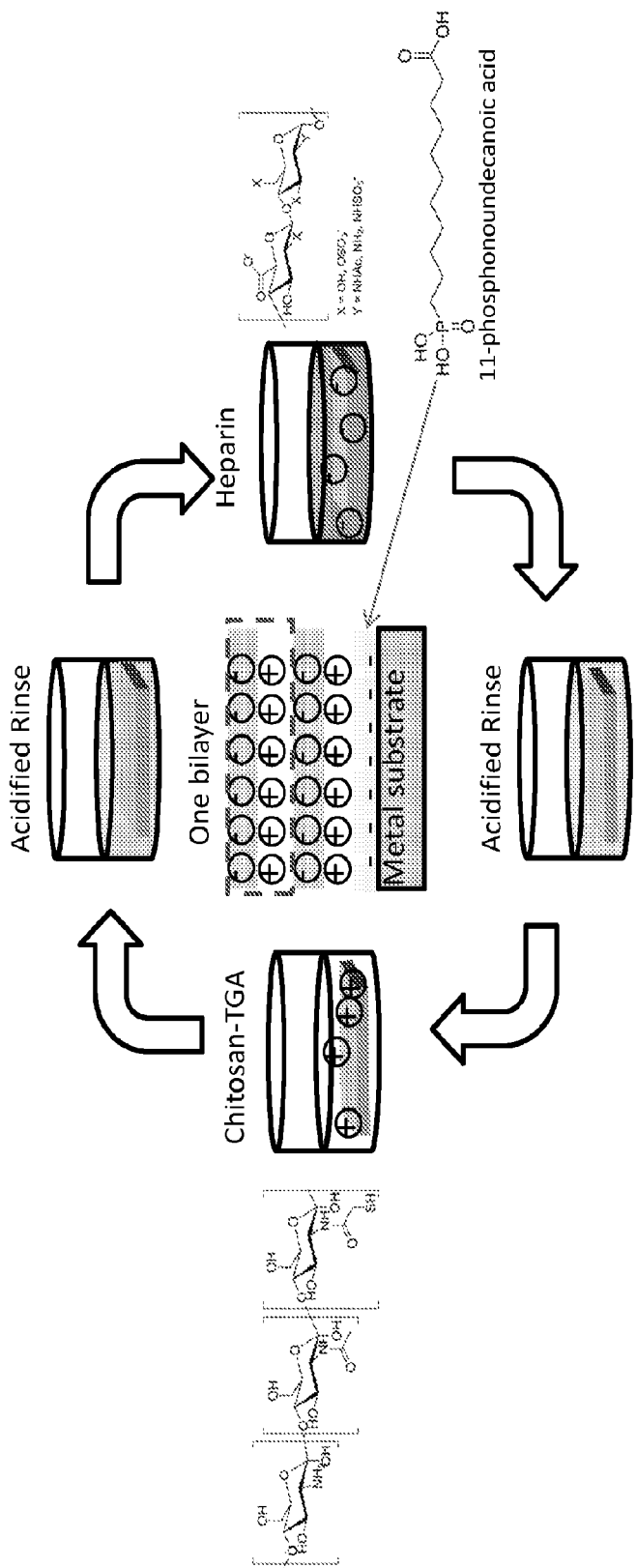
FIG. 11 is a schematic illustration of the LBL coating method.

Layer-by-Layer Coating Method: As shown schematically in FIG. 11, the metal substrates were first modified with a self-assembled monolayer of 11-phosphonoundecanoic acid (11-PUA). Then beginning with chitosan-thioglycolic acid (chitosan-TGA), alternating coatings of chitosan-TGA and heparin were deposited onto the substrate until the desired number of bilayers was reached.

Nitrosation: The materials described in the foregoing, however, do not release NO without further modification. In order for them to do this, the chitosan-TGA must be nitrosated. This can be done either before or after coating using the LBL method.

For example, to nitrosate the chitosan-TGA before coating: chitosan-TGA is combined with tert-Butyl nitrite and methanol and stirred overnight, placed under vacuum for 3 hours, and then the substrates are coated using the LBL method.

To nitrosate the chitosan-TGA after coating: the LBL-coated substrates are combined with tert-Butyl nitrite and methanol, stirred overnight, and placed under vacuum for 3 hours.

Figure 12:
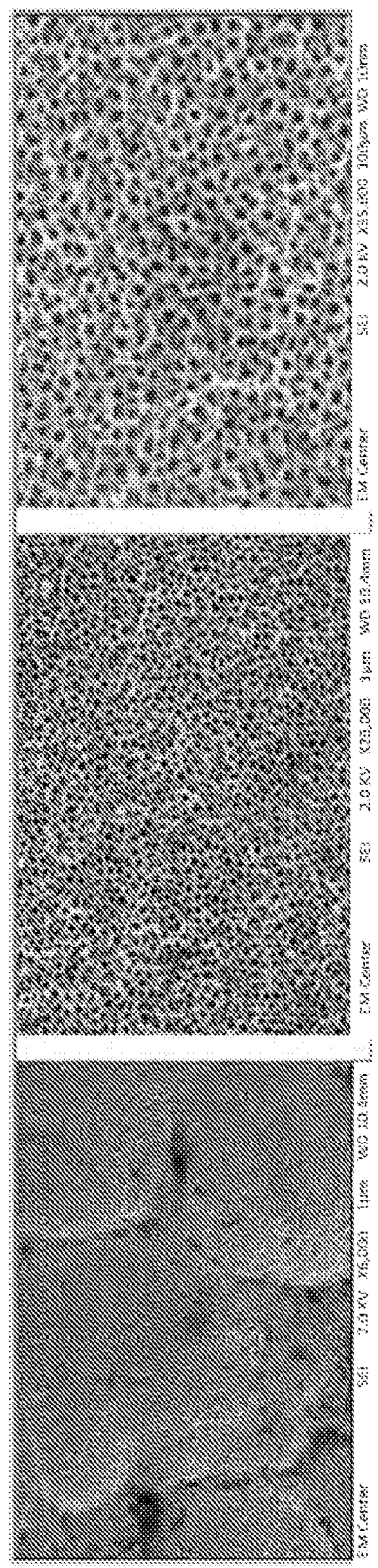
FIG. 12 is a series of three SEM images obtained of titanium-nanotube LBL-coated substrates (from left: 6,000×, 20,000×; and 35,000×).

SEM: Resulting surfaces can be and were evaluated using a scanning electron microscope (SEM) to observe the surface texture. FIG. 12 is a series of three SEM images obtained of titanium-nanotube LBL-coated substrates (from left: 6,000×, 20,000×; and 35,000×). The resulting surface textures were not changed by the placement of nitrosation before or after coating.

Figure 13:
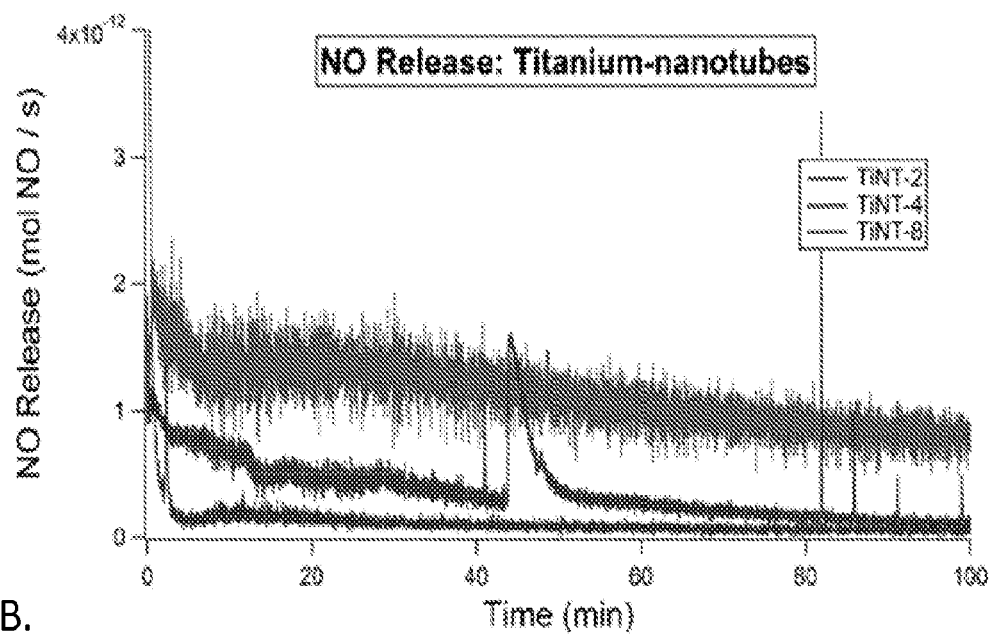
FIG. 13, upper panel is a graph of NO release over time from titanium-nanotube substrate samples; lower panel is a graph of NO release over time from stainless steel 316 substrate samples.
Figure 13:
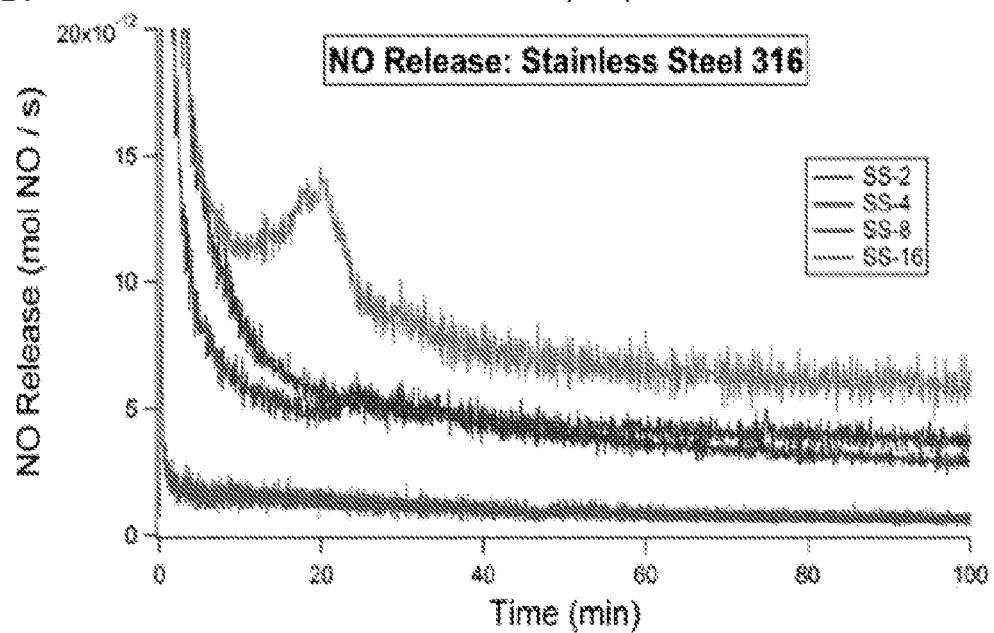

NO Release Measurements: Using a Nitric oxide Analyzer (NOA), samples were tested to determine NO release per second. Samples were run at 37° C. in phosphate buffer saline (PBS) with a pH 7.40 to imitate blood conditions in the human body. FIG. 13A (upper panel) is a graph of NO release over time from titanium-nanotube samples. FIG. 13B (lower panel) is a graph of NO release over time from stainless steel 316 samples. The different colored data readings identify the number of layers in the sample, according to the inset at right in each figure.

Effect of Nitrosation: 2 bilayers were applied onto titanium nanotubes. The surfaces were nitrosated either before or after application. No measureable release of NO was observed from samples for which nitrosating occurred before coating. NO release was observed from samples for which nitrosating occurred after coating.

Effect of Bilayer Number: 2, 4 and 8 bilayers were applied onto titanium nanotubes. The number of bilayers was inversely proportional to the NO release. 2, 4, 8 and 16 bilayers were applied to flat stainless steel substrates. The number of bilayers was proportional to the NO release.

The results demonstrate success of a layer-by-layer coating method in creating polyelectrolyte multilayers. Coated surfaces were shown to release nitric oxide. NO release and surface structure were characterized for both stainless steel 316 and titanium-nanotube substrates. Results are summarized in Table 1 below.

TABLE 1

| Results | PEM Coating | Substrate Type | Nitrosation Placement | Number of Bilayers |
|---|---|---|---|---|
| Affects surface structure? | YES | — | NO | NO |
| Affects amount of NO released? | YES | YES | YES | YES |

Resulting substrate samples and devices such as stents made of the substrate materials as described above are further tested for platelet activation using a method for assaying platelet activation upon contact of the substrate with a blood sample. Such methods include: i) use of a platelet aggregometer and a functional index such as an index of spontaneous aggregation, or of aggregation response to ADP, collagen, epinephrine, thrombin, or the like; (ii) an adhesion functional index, based on measurement of relative adhesion to a substratum, which could be a sample substrate; iii) Flow cytometry, detecting expression of glycoproteins; and iv) use of soluble markers such as beta thromboglobulin, platelet Factor 4, soluble P selectin, soluble glycoprotein V, and thromboxane(s).

What is claimed is:

1. A medical device for promoting endothelialization comprising:
   a body having at least a first surface;
   a plurality of nanotubes formed on the first surface of the body;
   at least one polyelectrolyte layer deposited on the nanotubes comprising: a polycation layer; and
   a polyanion layer,
   wherein the nanotubes and the polyelectrolyte layers form a nanopatterned structure on the first surface of the body of the medical device to promote endothelialization and reduce platelet adhesion and activation.

2. The medical device of claim 1, wherein the medical device is a vascular stent.

3. The medical device of claim 1, wherein at least one of the polycation or polyanion comprises nitric oxide-releasing groups.

4. The medical device of claim 3, wherein the device releases nitric oxide from the surface.

5. The medical device of claim 4, wherein the device releases nitric oxide at a rate of about 5 nmol/s to about 500 nmol/s.

6. The medical device of claim 5, wherein the device releases nitric oxide for a period of at least about 2 to about 3 weeks.

7. The medical device of claim 3, wherein the polycation comprises nitric oxide-releasing groups.

8. The medical device of claim 3, wherein the polyanion comprises nitric oxide-releasing groups.

9. The medical device of claim 1, wherein the nanotubes comprise titanium, a titanium alloy, a titanium oxide, or stainless steel.

10. The medical device of claim 1, wherein the polycation is chitosan.

11. The medical device of claim 1, wherein the polyanion is a glycosaminoglycan.

12. The medical device of claim 11, wherein the glycosaminoglycan is selected from heparin, heparan sulfate, chondroitin sulfate, keratan sulfate, dextran sulfate, a sulfated polysaccharide, and a sulfate-containing polyelectrolyte.

13. The medical device of claim 1, further comprising a growth factor adsorbed on the at least one polyelectrolyte layer.

14. The medical device of claim 13, wherein the growth factor is vascular endothelial growth factor (VEGF).

15. A method of promoting endothelialization and reducing platelet adhesion and activation in a tissue in a subject in need thereof, the method comprising:
   implanting a medical device in the tissue, wherein the device comprises: a body having at least a first surface;
   a plurality of nanotubes formed on the first surface of the body;
   at least one polyelectrolyte layer deposited on the nanotubes comprising:
   a polycation layer; and a polyanion layer,
wherein the nanotubes and the polyelectrolyte layers form a nanopatterned structure on the first surface of the body of the medical device to promote endothelialization and reduce platelet adhesion and activation.

16. The method of claim 15, wherein the medical device is a vascular stent.

17. The method of claim 15, wherein at least one of the polycation or polyanion comprises nitric oxide-releasing groups.

18. The method of claim 17, wherein the surface of the device releases nitric oxide over a period of time.

19. The medical device of claim 18, wherein the device releases nitric oxide at a rate of about 5 nmol/s to about 500 nmol/s.

20. The medical device of claim 19, wherein the device releases nitric oxide for a period of at least about 2 to about 3 weeks.

21. The method of claim 15, wherein the polycation comprises nitric oxide-releasing groups.

22. The method of claim 15, wherein the polyanion comprises nitric oxide-releasing groups.

23. The method of claim 15, wherein the nanotubes comprise titanium, a titanium alloy, a titanium oxide, or stainless steel.

24. The method of claim 15, wherein the polycation is chitosan.

25. The method of claim 15, wherein the polyanion is a glycosaminoglycan.

26. The method of claim 25, wherein the glycosaminoglycan is selected from heparin, heparan sulfate, chondroitin sulfate, keratan sulfate, dextran sulfate, a sulfated polysaccharide, and a sulfate-containing polyelectrolyte.

27. The method of claim 15, wherein the medical device further comprises a growth factor adsorbed on to the at least one polyelectrolyte layer.

28. The method of claim 27, wherein the growth factor is VEGF.

29. A method of modifying a surface of a medical device to promote (re)endothelialization and reduce platelet adhesion and activation, the method comprising:
forming nanotubes on at least a first surface of the medical device and depositing at least one polyelectrolyte layer on the nanotubes comprising:
depositing a polycation layer on the nanotubes;
rinsing the surface;
depositing a polyanion layer on the nanotubes; and
rinsing the surface,
wherein the nanotubes and the polyelectrolyte layers form a nanopatterned structure on the first surface of the medical device to promote (re)endothelialization and reduce platelet adhesion and activation.

30. The method of claim 29, further comprising modifying at least one of the polycation or the polyanion with nitric oxide-releasing groups.

31. The method of claim 30, wherein the surface of the device releases nitric oxide over a period of time.

32. The medical device of claim 31, wherein the device releases nitric oxide at a rate of about 5 nmol/s to about 500 nmol/s.

33. The medical device of claim 32, wherein the device releases nitric oxide for a period of at least about 2 to about 3 weeks.

34. The method of claim 29, wherein forming the nanotubes comprises anodizing the first surface of the medical device.

35. The method of claim 29, further comprising repeating the alternation of the polycation layer and polyanion layer until a desired thickness is reached.

36. The method of claim 29, wherein the nanotubes comprise titanium, a titanium alloy, a titanium oxide, or stainless steel.

37. The method of claim 29, wherein the polycation is chitosan.

38. The method of claim 29, wherein the polyanion is selected from heparin, heparan sulfate, and chondroitin sulfate.

39. The method of claim 29, further comprising adsorbing VEGF to the polyelectrolyte layers.

* * * * *